United States Patent
Grunewald (12) 
(10) Patent No.: US 9,592,091 B2
(45) Date of Patent: Mar. 14, 2017

(54) ABLATION CATHETER FOR VEIN ANATOMIES

(75) Inventor: Debby Grunewald, Los Angeles, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 1014 days.

(21) Appl. No.: 13/221,748

(22) Filed: Aug. 30, 2011

(65) Prior Publication Data

US 2013/0053841 A1     Feb. 28, 2013

(51) Int. Cl.
| | |
|---|---|
| A61B 18/12 | (2006.01) |
| A61B 18/14 | (2006.01) |
| A61B 17/00 | (2006.01) |
| A61B 18/00 | (2006.01) |

(52) U.S. Cl.
CPC ..... *A61B 18/1492* (2013.01); *A61B 2017/00084* (2013.01); *A61B 2017/00243* (2013.01); *A61B 2017/00867* (2013.01); *A61B 2018/00035* (2013.01); *A61B 2018/00065* (2013.01); *A61B 2018/00375* (2013.01); *A61B 2018/00577* (2013.01); *A61B 2018/1467* (2013.01); *A61B 2018/1472* (2013.01)

(58) Field of Classification Search
CPC ...... A61B 18/1492; A61B 2017/00243; A61B 2017/00867; A61B 2018/00375; A61B 2018/00577; A61B 2018/1467; A61B 2018/1472
USPC .............................................. 606/27, 34, 41
See application file for complete search history.

(56) References Cited

U.S. PATENT DOCUMENTS

| | | | |
|---|---|---|---|
| RE34,502 E | | 1/1994 | Webster, Jr. |
| 5,327,905 A | * | 7/1994 | Avitall ...................... 600/585 |
| 5,329,923 A | | 7/1994 | Lindquist |
| 5,391,199 A | | 2/1995 | Ben-Haim |
| 5,443,489 A | | 8/1995 | Ben-Haim |
| 5,480,422 A | | 1/1996 | Ben-Haim |
| 5,546,951 A | | 8/1996 | Ben-Haim |
| 5,558,091 A | | 9/1996 | Acker et al. |
| 5,568,809 A | | 10/1996 | Ben-Haim |
| 5,642,736 A | | 7/1997 | Avitall |
| 5,755,760 A | | 5/1998 | Maguire et al. |
| 5,779,669 A | | 7/1998 | Haissaguerre et al. |

(Continued)

FOREIGN PATENT DOCUMENTS

| | | |
|---|---|---|
| CN | 101304778 A | 11/2008 |
| CN | 101647725 A | 2/2010 |

(Continued)

OTHER PUBLICATIONS

Extended European Search Report dated Nov. 19, 2012 for EP application No. 12182244.9 (6 pages).

(Continued)

*Primary Examiner* — Daniel Fowler
(74) *Attorney, Agent, or Firm* — Lewis Roca Rothgerber Christie LLP (57) ABSTRACT

A catheter adapted for simultaneous tissue contact with two opposing ring electrodes carried on a generally linear portion of an electrode assembly is adapted to straddle an ostium for ablating two lesions along a chord of the ostium, wherein the generally linear portion is stabilized on the ostium to ensure proper tissue contact when a force is applied down the length of the catheter body.

17 Claims, 9 Drawing Sheets

(56) References Cited

U.S. PATENT DOCUMENTS

| | | | |
|---|---|---|---|
| 5,800,428 A | 9/1998 | Nelson et al. | |
| 5,897,529 A | 4/1999 | Ponzi | |
| 5,961,513 A | 10/1999 | Swanson et al. | |
| 5,964,757 A | 10/1999 | Ponzi | |
| 6,064,902 A | 5/2000 | Haissaguerre et al. | |
| 6,071,274 A * | 6/2000 | Thompson et al. | 604/528 |
| 6,090,104 A | 7/2000 | Webster, Jr. | |
| 6,120,476 A | 9/2000 | Fung et al. | |
| 6,123,699 A | 9/2000 | Webster, Jr. | |
| 6,161,543 A | 12/2000 | Cox et al. | |
| 6,171,277 B1 | 1/2001 | Ponzi | |
| 6,183,435 B1 | 2/2001 | Bumbalough et al. | |
| 6,183,463 B1 | 2/2001 | Webster, Jr. | |
| 6,198,974 B1 | 3/2001 | Webster, Jr. | |
| 6,203,525 B1 | 3/2001 | Whayne et al. | |
| 6,210,407 B1 | 4/2001 | Webster | |
| 6,217,528 B1 * | 4/2001 | Koblish et al. | 600/585 |
| 6,267,746 B1 | 7/2001 | Bumbalough | |
| 6,325,797 B1 * | 12/2001 | Stewart et al. | 606/41 |
| 6,371,955 B1 | 4/2002 | Fuimaono et al. | |
| 6,468,260 B1 | 10/2002 | Bumbalough et al. | |
| 6,500,167 B1 | 12/2002 | Webster, Jr. | |
| 6,522,933 B2 | 2/2003 | Nguyen | |
| 6,527,769 B2 | 3/2003 | Langberg et al. | |
| 6,592,581 B2 | 7/2003 | Bowe | |
| 6,628,976 B1 | 9/2003 | Fuimaono et al. | |
| 6,650,920 B2 * | 11/2003 | Schaldach et al. | 600/374 |
| 6,669,693 B2 | 12/2003 | Friedman | |
| 6,949,097 B2 | 9/2005 | Stewart et al. | |
| 6,955,675 B2 | 10/2005 | Jain | |
| 7,097,643 B2 | 8/2006 | Cornelius et al. | |
| 7,311,705 B2 | 12/2007 | Sra | |
| 7,588,568 B2 | 9/2009 | Fuimaono et al. | |
| 2002/0045809 A1 | 4/2002 | Ben-Haim | |
| 2003/0060822 A1 | 3/2003 | Schaer et al. | |
| 2005/0015082 A1 | 1/2005 | O'Sullivan et al. | |
| 2006/0253116 A1 | 11/2006 | Avitall et al. | |
| 2007/0066878 A1 | 3/2007 | Worley et al. | |
| 2007/0173812 A1 | 7/2007 | Bonan et al. | |
| 2010/0168548 A1 | 7/2010 | Govari et al. | |
| 2012/0143008 A1 | 6/2012 | Wilkins et al. | |
| 2012/0172703 A1 | 7/2012 | Esguerra et al. | |
| 2013/0006238 A1 | 1/2013 | Ditter et al. | |

FOREIGN PATENT DOCUMENTS

| | | |
|---|---|---|
| EP | 1 382 310 A2 | 1/2004 |
| EP | 1 498 080 A1 | 1/2005 |
| JP | 2001-519199 A | 10/2001 |
| JP | 2005-46623 A | 2/2005 |
| JP | 2009-508589 A | 3/2009 |
| WO | WO 95/02995 | 2/1995 |
| WO | WO 96/05758 | 2/1996 |
| WO | WO 96/05768 | 2/1996 |
| WO | WO 97/24983 | 7/1997 |
| WO | WO 98/29033 | 7/1998 |
| WO | WO 99/18878 | 4/1999 |

OTHER PUBLICATIONS

Haïssaguerre, et al. "Spontaneous Initiation of Atrial Fibrillation by Ectopic Beats Originating in the Pulmonary Veins," *The New England Journal of Medicine*, vol. 339 No. 10, pp. 659-666, Sep. 3, 1998.

European Search Report dated Dec. 2, 2004 for corresponding European Application No. 04254306.6, 4 pages.

AU Patent Examination Report No, 2, dated Jun. 24, 2015 for AU Patent Application No. 2012213929, 3 pages.

SIPO Search Report dated Aug. 25, 2015 in corresponding CN Application No. 201210316424.X, 3 pages.

English translation of Japanese Patent Office action dated May 31, 2016 in corresponding JP Application No. 2012-188338, 4 pages.

\* cited by examiner

ABLATION CATHETER FOR VEIN ANATOMIES

FIELD OF INVENTION

This invention relates generally to methods and devices for invasive medical treatment, and specifically to catheters, in particular, irrigated ablation catheters.

BACKGROUND

Ablation of myocardial tissue is well known as a treatment for cardiac arrhythmias. In radio-frequency (RF) ablation, for example a catheter is inserted into the heart and brought into contact with tissue at a target location. RF energy is then applied through electrodes on the catheter in order to create a lesion for the purpose of breaking arrhythmogenic current paths in the tissue. Specifically, atrial fibrillation is an abnormal heart rhythm originating in the atria (top chambers of the heart). Instead of the impulse traveling in an orderly fashion through the heart, many impulses begin and spread through the atria, causing a rapid and disorganized heartbeat. Ablation of the four pulmonary veins, also known as "Pulmonary Vein Isolation" (PVI), using a circumferential mapping technique is proving to be successful for many patients with atrial fibrillation.

The ablation is performed by delivering energy from a catheter to the area of the atria that connects to the pulmonary vein ostia, producing a circular scar or lesion around the ostium.

The lesion then blocks any impulses firing from within the pulmonary vein, thus preventing atrial fibrillation from occurring. The process is typically repeated to all four pulmonary veins.

Ablation has been accomplished primarily by means of focal ablation, that is, ablation by a tip electrode at a distal end of the catheter. Thus, for linear ablation along a line or curve, the tip electrode is repositioned repeatedly or dragged across the tissue along the line or curve during a prolonged ablation. Repositioning or dragging is time-consuming and proper tissue contact is often difficult to achieve when maneuvering in the small confines of the atria. Also known are irrigated ablation tip and ring electrodes which are effective at reducing electrode temperature during ablation to minimize the formation of char and coagulum. However, fluid load on the patient is a concern, especially where multiple electrodes are being irrigated.

Accordingly, there is a desire for a catheter adapted for PVI procedures regardless of ostium shape or size that would improve catheter maneuverability and targeting of the ostia which would in turn improve lesion formation and shorten duration of ablation procedures. In particular, there is a desire for a catheter with multiple ring electrodes that can ensure greater and more stable tissue contact with the ostium by enabling two simultaneous contact locations between the ring electrodes and the ostium.

SUMMARY OF THE INVENTION

The present invention is directed to an irrigated ablation catheter having an electrode assembly adapted for vein anatomies and related procedures, including pulmonary vein isolation (PVI). The electrode assembly has an elongated or linear portion carrying a plurality of ring electrodes (or ring electrode arrays). The length of the linear portion spans the vein diameter so that the linear portion can be pressed against the ostium with at least two ring electrodes in simultaneous contact with the ostium. With proper contact verified by ECG readings and fluoroscopy, the ring electrodes are selectively energized for ablation in a unipolar and/or bipolar fashion to create lesions in accomplishing isolation of the pulmonary veins.

With a plurality of ring electrodes on the linear portion, electrode(s) can be selectively energized to perform ablation via a controller or switch box in an RF generator. Any electrode(s) that are determined to be in proper contact and position with the ostium based on ECG data are used to perform the ablation. To completely entrap a vein with a generally continuous circumferential lesion, the catheter can be rotated incrementally until a 180 degree rotation is completed. During the incremental rotations, two lesions can be created, one at each of two contacting electrodes, each lesion being across the ostium from the other lesion. With a plurality of ring electrodes arranged as a first and a second groups or arrays at or near the distal and proximal ends of the linear portion, the electrode assembly is adapted for PVI regardless of most vein shape or size. In fact, the catheter of the present invention can be used to perform ablation on all vein anatomies, including common ostia.

In one embodiment, a catheter of the present invention includes an elongated body and a distal electrode assembly that includes a generally linear distal portion and a generally linear proximal portion, the distal portion have a greater length than the proximal portion, the proximal and distal portions being connected by a U-shaped portion and the proximal portion being connected to the catheter by an elbow connector portion. The distal and proximal portions are generally aligned with each other and generally perpendicular to the longitudinal axis of the catheter. The catheter may also include an intermediate deflection portion proximal the electrode assembly for enabling uni or bi-directional deflection of the electrode assembly.

In a detailed embodiment, the entirety of the distal electrode assembly, inclusive of the generally linear distal and proximal portions, the U-shaped portion and the elbow connecting portion, generally lies within a single common plane.

In another detailed embodiment, the elbow connecting portion has an angle ranging between about 30 and 120 degrees, and more preferably about 90 degrees.

In another detailed embodiment, the electrode assembly carries a plurality of ring electrodes ranging between about two and twelve, preferably between about four and eight, and more preferably about six electrodes, wherein a group or array of ring electrodes is mounted at or near the distal end of the generally linear distal portion and another group or array of ring electrodes is mounted at or near the proximal end of the generally linear distal portion.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

DETAILED DESCRIPTION OF THE INVENTION

A catheter of the present invention is adapted for deployment in a target region of the body, e.g., the atria of the heart, and designed to facilitate ablation at or near a vein anatomy, such as a PV ostium, by means of radiofrequency (RF) current. The catheter is advantageously designed for pulmonary vein isolation by means of RF lesion(s) at generally opposing locations generally along any chord (two locations on a circumference) or a diameter of the ostium. By providing an elongated or generally linear portion carrying a plurality of ring electrodes that can straddle the ostium for simultaneously contacting the ostium at two locations across the ostium, the catheter can remain in relatively stable position once placed on the ostium as supported at the two contact locations to receive an applied normal force along the longitudinal length of the catheter to ensure proper contact between at least two ring electrodes and the ostium. With the use of ECG readings and fluoroscopy, an operator can operate the catheter to deliver RF energy through one or more selected ring electrodes in contact with the ostium as uni-polar electrodes to the contacting tissue of the ostium to a return electrode (e.g., an external electrode patch affixed to the patient's back) to accomplish focal uni-polar lesions. If appropriate or desired, selected ring electrodes in contact with the ostium can also be energized as bi-polar electrodes to form bi-polar lesions between the energized ring electrodes. Thus, energy can be applied to any singular electrode from a pair of any two electrodes, or from multiple pairs of electrodes. And, by rotating the catheter about its longitudinal axis, different discreet or continuous locations along the circumference of the ostium can be ablated in this manner.

Figure 1:
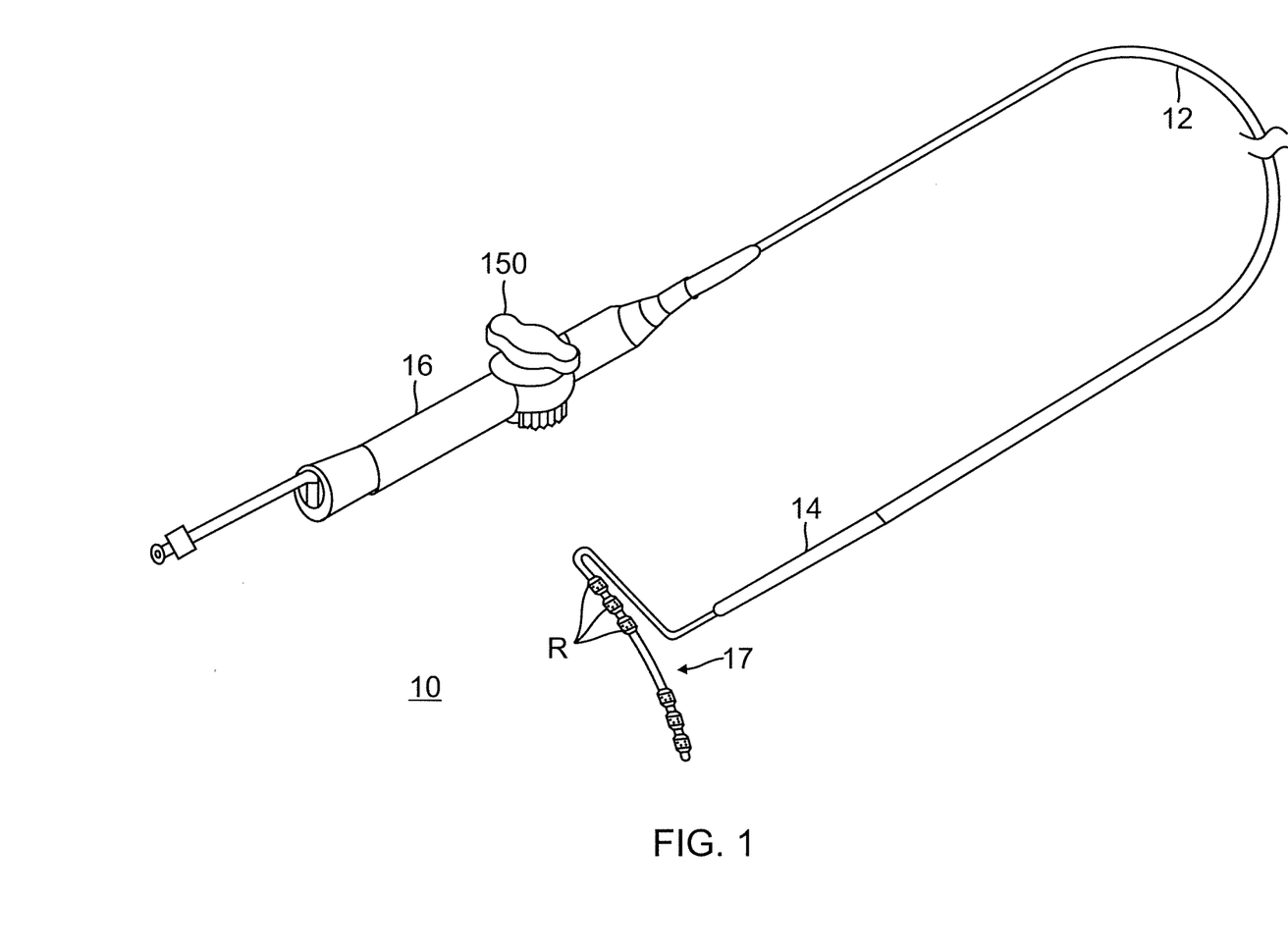
FIG. 1 is a perspective view of an embodiment of a catheter in accordance with the present invention.
Figure 2:
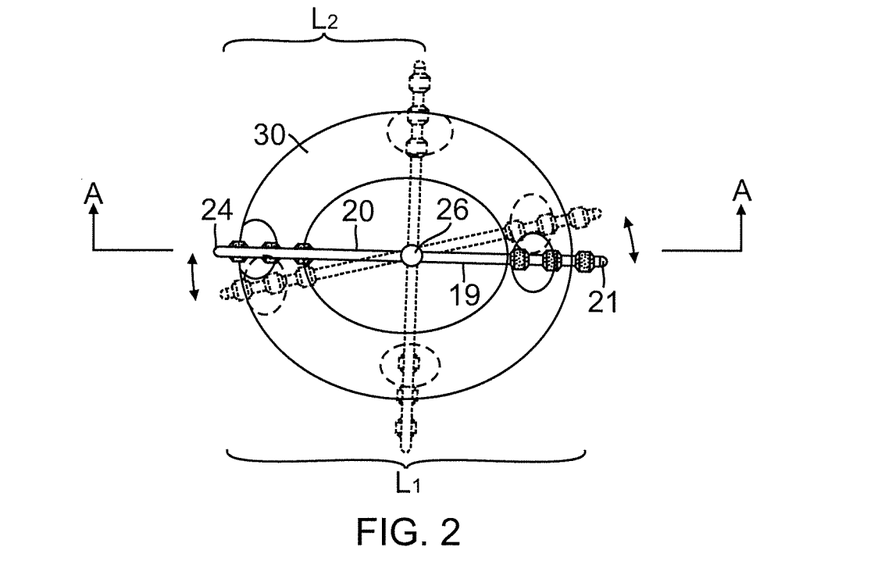
FIG. 2 is a top plan view of a portion of the catheter of FIG. 1 in position on an ostium.
Figure 3:
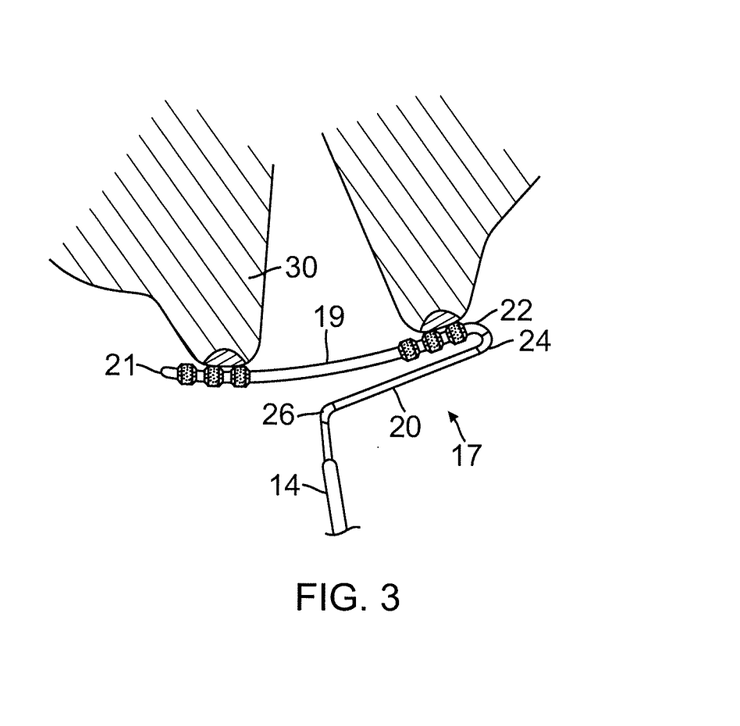
FIG. 3 is side-elevational view of the catheter and an ostium of FIG. 2, taken along line A-A.

As illustrated in FIGS. 1, 2 and 3, the present invention includes a steerable catheter 10 with a distal electrode assembly 17 that includes a generally elongated or linear distal portion 19 having a first predetermined length L1, a free distal end 21, and a proximal end 22 that is attached to the catheter by a U-shaped portion 24. The assembly also includes a generally elongated or linear proximal portion 20 having a second predetermined length L2 lesser than the first predetermined length L1, wherein the linear distal and proximal portions 19 and 20 are generally perpendicular to the longitudinal axis of the catheter by means of an elbow connecting portion 26 attached to a proximal end of the generally linear proximal portion 20. The entirety of the distal electrode assembly 17, inclusive of the generally linear distal and proximal portions 19 and 20, the U-shaped portion 24 and the elbow connecting portion 26, can generally lie within a single common plane.

The electrode assembly 17 is flexible with shape memory so that it is biased to assume a predetermined shape but can temporarily assume another shape under an applied force and return to the predetermined shape when the applied force is removed. Irrigated ablation ring electrodes R are mounted on the assembly 17 so as to contact generally opposing locations along any chord or a diameter of an ostium 30 (FIGS. 2 and 3). In the illustrated embodiments, either or both of the linear distal and proximal portions 19 and 20 may be slightly curved, e.g., either or both slightly concave or convex, so that flexure of portion(s) 19, 20 facilitates proper tissue contact with the ostium when a normal force N is applied along a longitudinal axis of the catheter. Furthermore, as shown in FIG. 2, the catheter can be rotated (clockwise or counterclockwise) about its longitudinal axis such that different locations along the circumference of the ostium can come into contact with the ring electrodes R for ablation. Such different locations can be discrete locations or overlapping to form a continuous lesion.

Referring to FIG. 1, the catheter 10 according to the disclosed embodiments comprises an elongated body that may include an insertion shaft or catheter body 12 having a longitudinal axis, and an intermediate section 14 distal of the catheter body that can be uni- or bi-directionally deflectable off-axis from the catheter body. Distal of the intermediate section 14 is the distal electrode assembly 17 carrying a plurality of ring electrodes R adapted for ablation and irrigation.

Figure 4A:
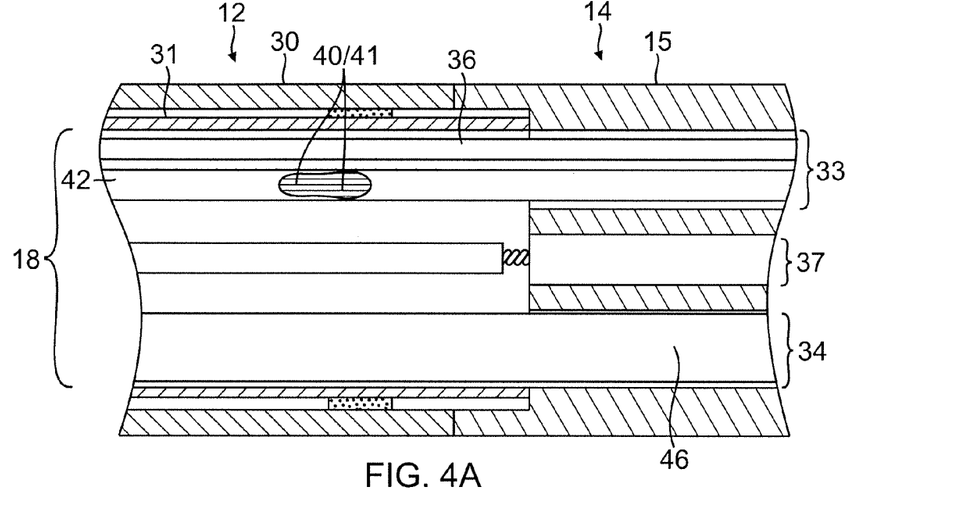
FIG. 4A is a side cross-sectional view of the catheter of FIG. 1, including a junction of a catheter body and an intermediate deflection section, taken alone one diameter.
Figure 4B:
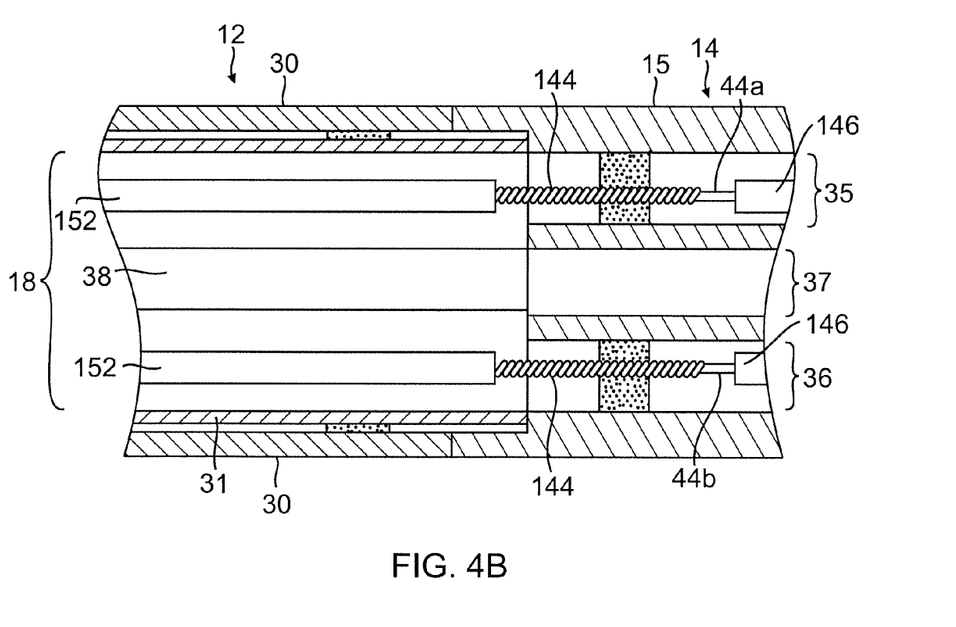
FIG. 4B is a side cross-sectional view of the catheter of FIG. 1, including a junction of a catheter body and an intermediate deflection section, taken along another diameter.
Figure 4C:
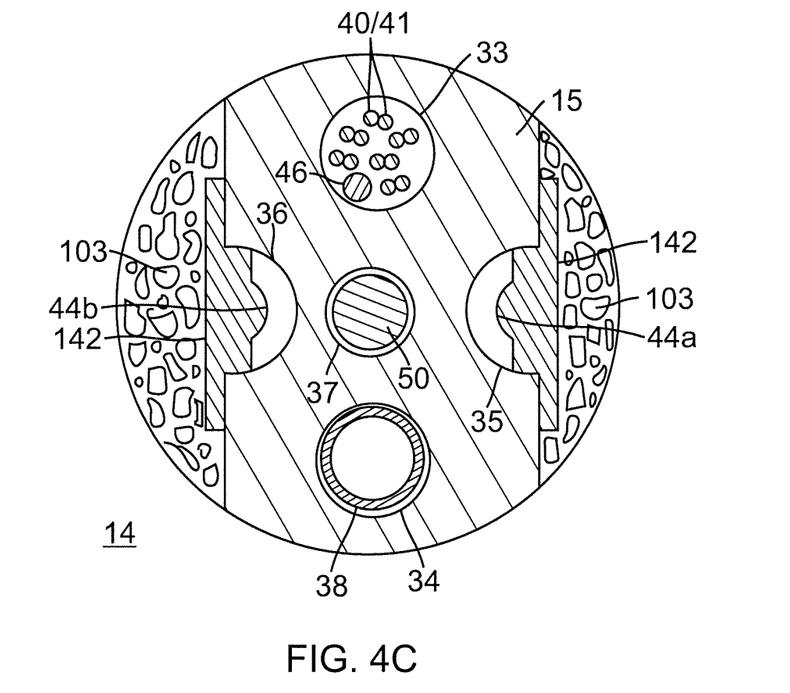
FIG. 4C is an end cross-sectional view of an embodiment of an intermediate deflection section of the catheter of FIG. 1.

In the depicted embodiment of FIGS. 4A, 4B and 4C, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 30 made of polyurethane or PEBAX. The outer wall 30 comprises an imbedded braided mesh of stainless steel or the like, as is generally known in the art, to increase torsional stiffness of the catheter body 12 so that, when the control handle 16 is rotated, the intermediate section 14 and distal section 17 will rotate in a corresponding manner.

The outer diameter of the catheter body 12 is not critical, but is preferably no more than about 8 french, more preferably 7 french. Likewise the thickness of the outer wall 30 is not critical, but is thin enough so that the central lumen 18 can accommodate any desired wires, cables and/or tubes. The inner surface of the outer wall 30 is lined with a stiffening tube 31 to provide improved torsional stability. The outer diameter of the stiffening tube 31 is about the same as or slightly smaller than the inner diameter of the outer wall 30. The stiffening tube 31 can be made of any suitable material, such as polyimide, which provides very good stiffness and does not soften at body temperature.

The deflectable intermediate section 14 comprises a short section of tubing 15 having multiple lumens, each occupied by the various components extending through the intermediate section. In the illustrated embodiment, there are five lumens 33, 34, 35, 36 and 37 as best seen in FIG. 4C. Lead wire/thermocouple pairs 40,41 for each ring electrode pass through a first off-axis lumen 33 in the illustrated embodiment. A nonconductive protective sheath may be provided. A cable 46 for a position sensor 48, including an assembly of single axis sensors (SASs) positioned on the distal assembly, also passes through the first lumen A fluid irrigation tubing 38 passes through a second, off-axis lumen 34. For at least uni-directional deflection, a first puller wire 44a passes through a third, off-axis lumen 35. For bi-directional deflection, a second puller wire 44b passes through a fourth, off-axis lumen 36. A proximal end of a shape memory support member 50 for the assembly 17 is potted or otherwise anchored within the fifth lumen 37 a short distance proximal of the distal end of the tubing 15.

The multi-lumened tubing 15 of the intermediate section 14 is made of a suitable non-toxic material that is preferably more flexible than the catheter body 12. A suitable material is braided polyurethane or PEBAX, i.e., polyurethane or PEBAX with an embedded mesh of braided stainless steel or the like. The plurality and size of each lumen are not critical, provided there is sufficient room to house the components extending therethrough. Position of each lumen is also not critical, except the positions of the lumens 35, 36 for the puller wires 44a, 44b. The lumens 35, 36 should be off-axis, and diametrically opposite of each other for bi-directional deflection along a plane.

The useful length of the catheter, i.e., that portion that can be inserted into the body can vary as desired. Preferably the useful length ranges from about 110 cm to about 120 cm. The length of the intermediate section 14 is a relatively small portion of the useful length, and preferably ranges from about 3.5 cm to about 10 cm, more preferably from about 5 cm to about 6.5 cm.

A preferred means for attaching the catheter body 12 to the intermediate section 14 is illustrated in FIGS. 4A and 4B. The proximal end of the intermediate section 14 comprises an inner circumferential notch that receives the outer surface of the distal end of the stiffening tube 31 of the catheter body 12. The intermediate section 14 and catheter body 12 are attached by glue or the like, for example, polyurethane. If desired, a spacer (not shown) can be provided within the catheter body 12 between the distal end of the stiffening tube 31 and the proximal end of the intermediate section 14 to provide a transition in flexibility at the junction of the catheter body 12 and the intermediate section, which allows the junction to bend smoothly without folding or kinking. An example of such a spacer is described in more detail in U.S. Pat. No. 5,964,757, the disclosure of which is incorporated herein by reference.

Figure 5A:
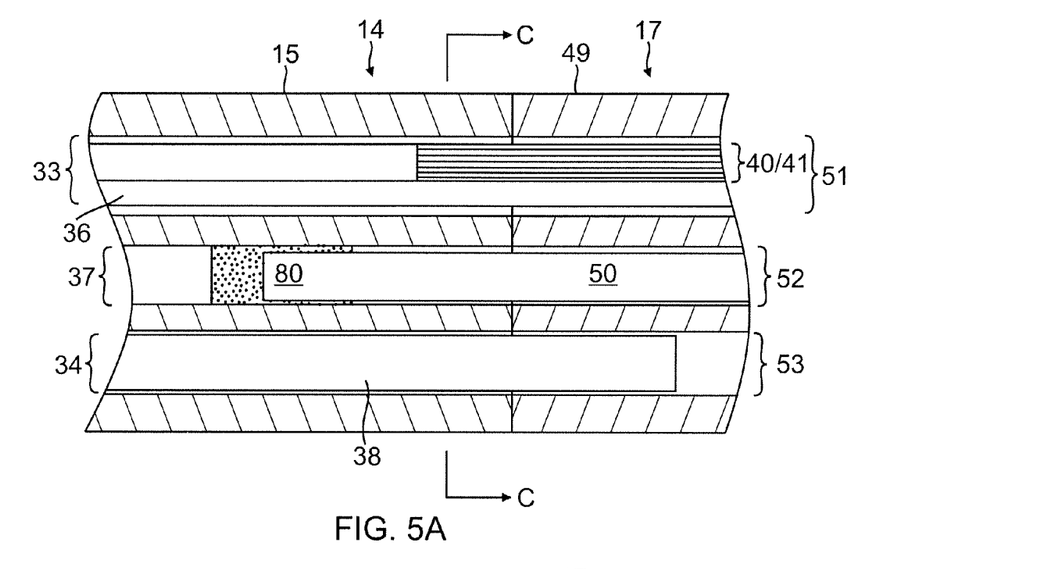
FIG. 5A is a side cross-sectional view of the catheter of FIG. 1, including a junction of an intermediate deflection section and a distal electrode assembly, taken along one diameter.
Figure 5B:
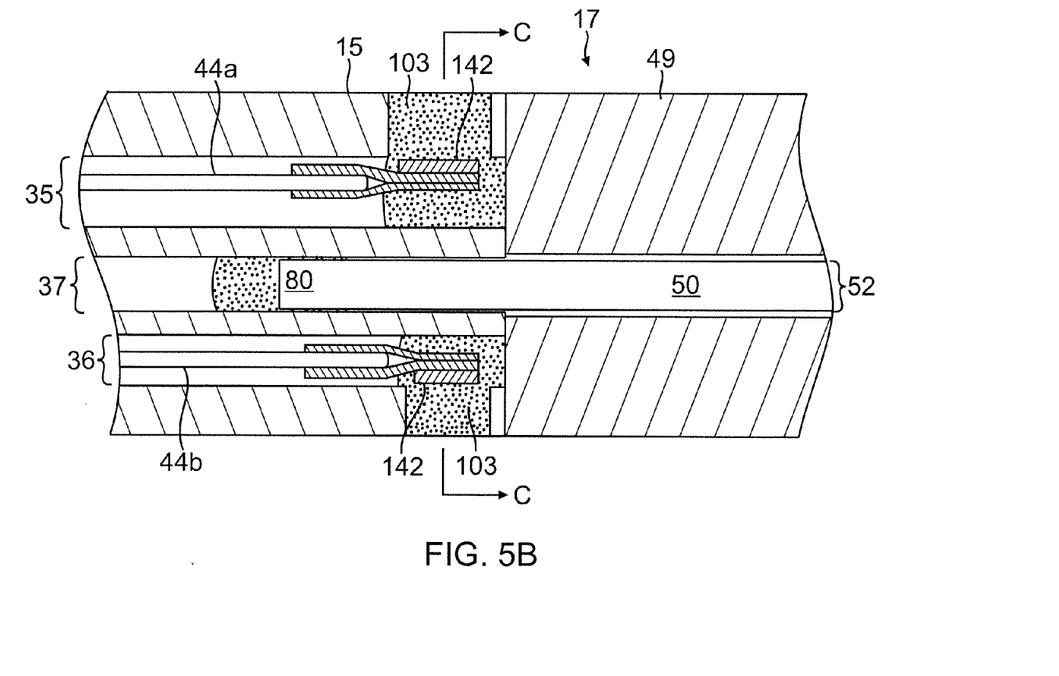
FIG. 5B is a side cross-sectional view of the catheter of FIG. 1, including a junction of an intermediate deflection section and a distal electrode assembly, taken along another diameter.
Figure 6A:
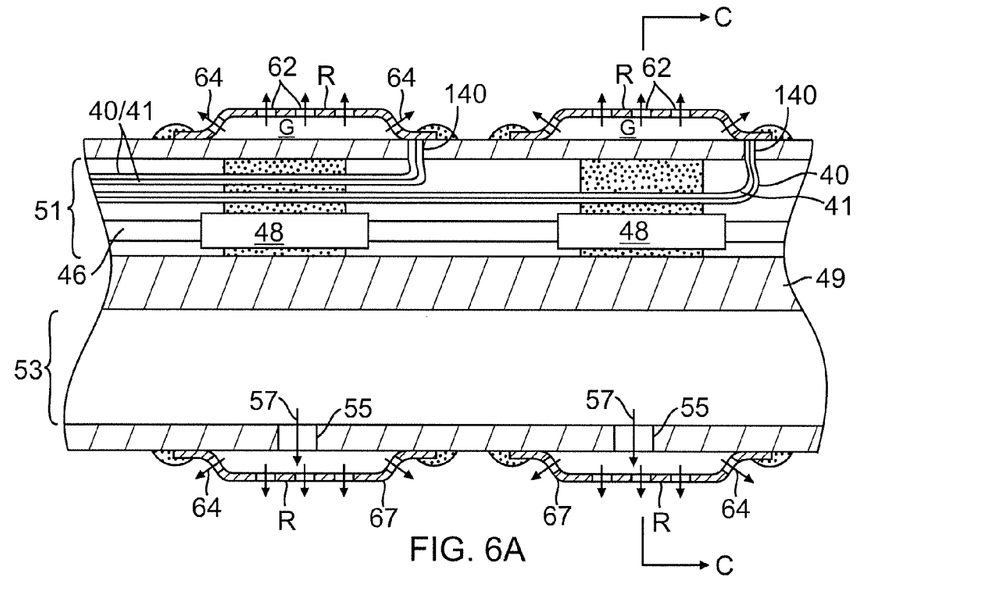
FIG. 6A is a side cross-sectional view of an electrode-carrying distal portion of the electrode assembly of FIG. 1, taken along a diameter.
Figure 6B:
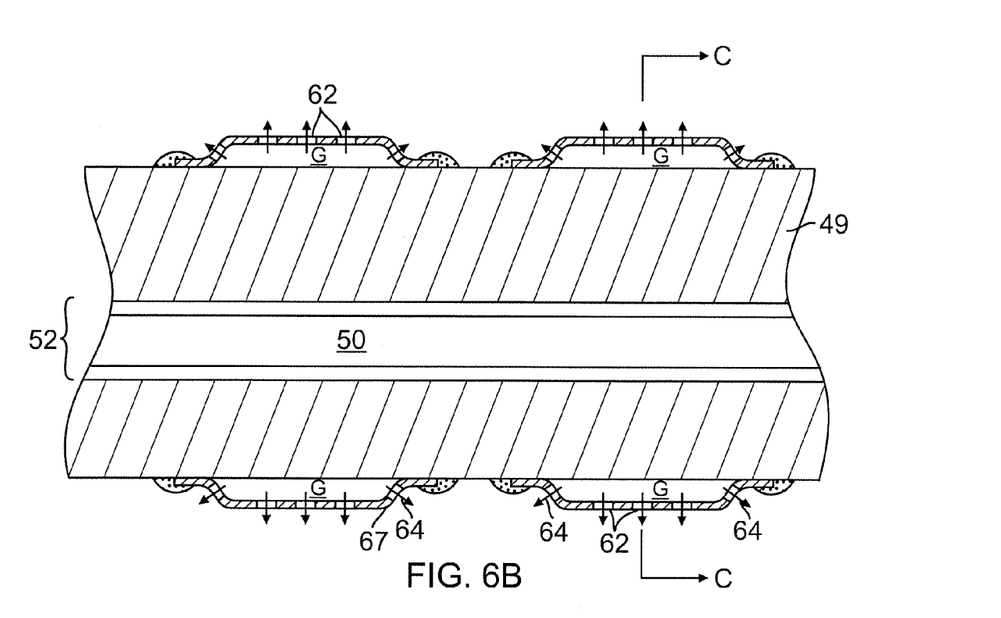
FIG. 6B is a side cross-sectional view of an electrode-carrying distal portion of the electrode assembly of FIG. 1, taken along another diameter.
Figure 6C:
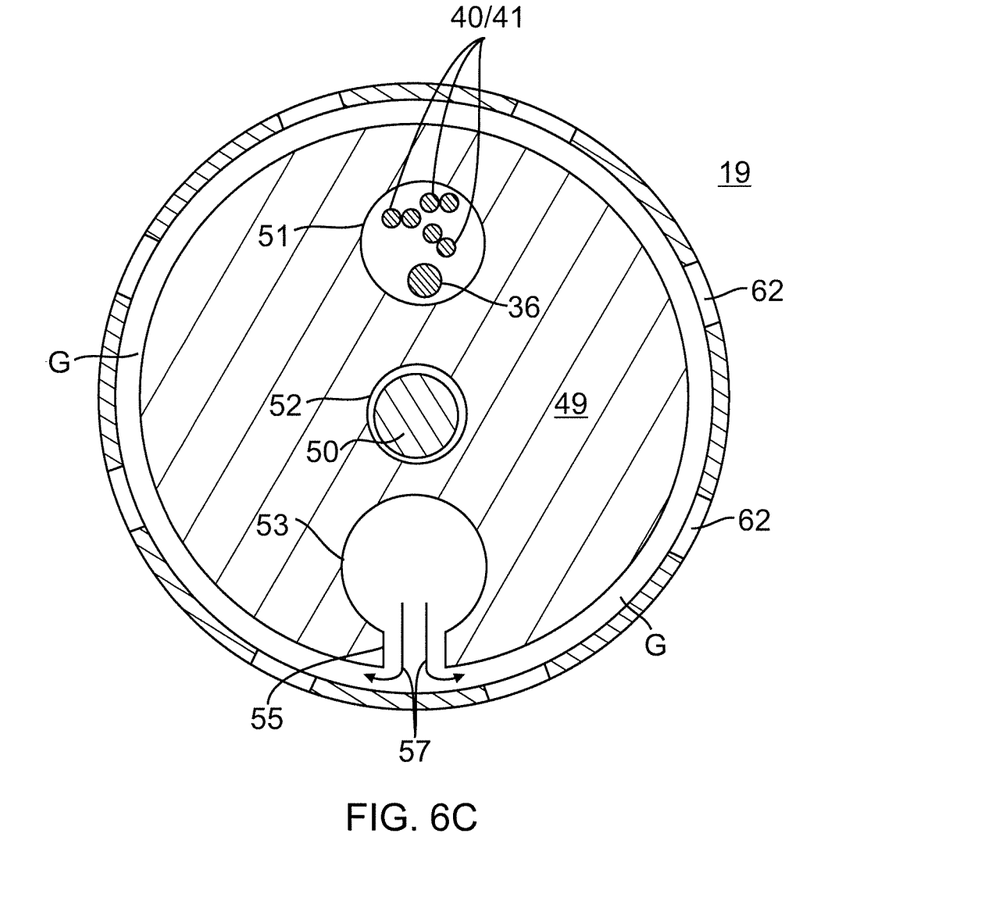
FIG. 6C is an end cross-sectional view of the electrode-carrying distal portion of FIGS. 6A and 6B, taken along line C-C.

With reference to FIGS. 5A, 5B and 6C, distal the intermediate section 14 is the distal electrode assembly 17 which includes a multi-lumened tubing 49. The tubing 49 can be made of any biocompatible plastic such as polyurethane or PEBAX. In the illustrated embodiment, the tubing 49 has three lumens 51, 52 and 53. The lead wire/thermocouple pairs 40, 41 for ring electrodes and the position sensor 48 (e.g., single axis sensors or SASs) along the cable 46 pass through a first, on-axis lumen 51 which is generally in axial alignment with the first lumen 33 of the intermediate section 14. A third, off-axis lumen 53 generally in axial alignment with the second lumen 34 of the intermediate section receives a distal end of the irrigation tubing 38. The tubing 38 is sized and/or potted with a sealant to form a fluid-tight seal in the lumen 53 so that fluid flows distally directly into the lumen 53. The shape memory support member 50 of the assembly 17 extends through a second lumen 52 generally in axial alignment with the fifth lumen 37 of the intermediate section 14.

As supported by the shape memory support member 50, which can be made of any suitable material with shape memory, including Nitinol, the distal electrode assembly 17, as illustrated in FIGS. 2 and 3, is configured with the generally linear distal portion 19 with the greater predetermined length L1, the U-shaped portion 24, the generally linear proximal portion 20 with the lesser predetermined length L2, and the elbow connecting portion 26, wherein the linear distal and proximal portions 19 and 20 are generally perpendicular to the longitudinal axis of the catheter. The generally linear distal and proximal portions 19 and 20 are generally aligned with each other such that the entirety of the assembly 17, inclusive of the generally linear distal and proximal portions, the U-shaped portion and the elbow connecting portion, can generally lie within a single common plane. This configuration facilitates the transfer of an applied force N down the catheter body to the generally linear distal portion 19 to ensure tissue contact at or near the distal and proximal ends 21, 22 of the generally linear distal portion 19.

Figure 7:
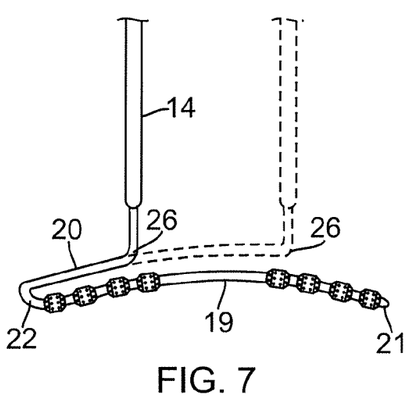
FIG. 7 is a side elevational view of alternate embodiments of a distal electrode assembly with an open configuration.

In the illustrated embodiment, the length L2 of the proximal portion 20 is about half of the length L1 of the distal portion 19 such that the elbow connecting portion 26 is at about a mid-location of the distal portion 19 such that the assembly 19 resembles a T-shape. However, as understood by one of ordinary skill in the art, the angle of approach to an ostium is not always perpendicular or "on axis" as shown in FIG. 3 so the length L2 of the proximal portion 20 can range between about ¼ to ¾ of the length L1 of the distal portion 20, as illustrated in FIG. 7, so that a normal force applied along the length of the catheter can effectively ensure tissue contact between the ring electrodes and the ostium. It is also understood by one of ordinary skill in the art that an angle α between two arms of the elbow connecting portion can vary beyond the approximately 90 degrees shown in FIG. 8. The angle α can range between about 30 to 120 degrees, as appropriate or desired.

An embodiment of a junction between the distal electrode assembly 17 and the intermediate deflection portion 14 is shown in FIGS. 5A and 5B. The shape memory support member 50 extends the entire length of the distal electrode assembly 17 with a proximal end 80 that extends into the lumen 37 of the intermediate deflection portion 14 and is anchored therein. A distal end of the shape memory support member terminates at the distal end of the tubing 49 of the assembly 17 whose end is sealed with an atraumatic plug of suitable biocompatible sealant material.

Figure 8:
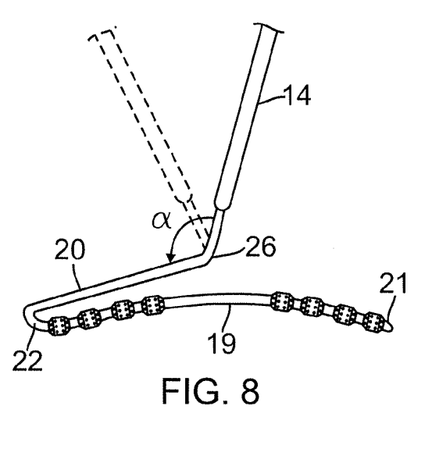
FIG. 8 is a side elevational view of additional alternate embodiments of a distal electrode assembly with an open configuration
Figure 9:
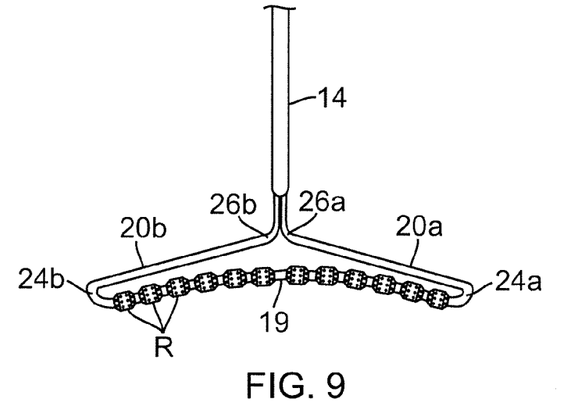
FIG. 9 is a side elevational view of yet additional alternate embodiments of a distal electrode assembly with a closed configuration.

The assembly 17 need not be an open configuration with a free distal end 21 as shown in the illustrated embodiment of FIGS. 3, 7 and 8. The present invention includes a closed configuration such as illustrated in FIG. 9, which includes a second generally linear proximal portion 20b, a second U-shaped portion 24b, and a second elbow connecting portion 26b. These second components mirror their counterparts in forming the assembly 17 as a closed configuration. In particular, the first and second elbow connecting portions 26a, 26b converge so that both proximal arms thereof extend into the distal end of the intermediate section 14. This closed configuration still provides a configuration by which two locations along any chord or a diameter of the ostium can simultaneously come in contact with the electrode assembly 17 and remain in a relatively stable position as a normal force is applied along the longitudinal axis of the catheter toward the ostium.

The distal portion 19 of the assembly 17 carries a plurality of ring electrodes R, for example, ranging between about two and twelve ring electrodes, arranged in spaced-apart groups or arrays at or near opposing ends 21 and 22 of the distal portion 19. In the disclosed embodiment, there are six ring electrodes arranged in two arrays of three within which the three electrodes are equally spaced from each other. However, it is understood that the ring electrodes need not be grouped distinguishably, that is, the generally linear distal portion 19 can carry a series of electrodes that are equally (or not equally) spaced from an adjacent electrode. Moreover, each group of electrodes need not have an equal number of electrodes.

As shown in FIGS. 6A, 6B and 6C, in the distal portion 19 of the assembly 17, a radial opening 55 is formed in the side wall of the tubing 49 underneath each ring electrode R so that fluid flows from the irrigation tubing into the lumen 53 of the tubing 49 and into the ring electrodes as shown by arrows 57. The size of the opening 55 in the tubing 49 can vary with the position along the length of the distal portion 19. For optimum flow, the more distal an opening 55 is along the distal portion 19, the greater the size or cross-section of the opening and/or the plurality of openings 55 under each ring electrode.

Figure 10:
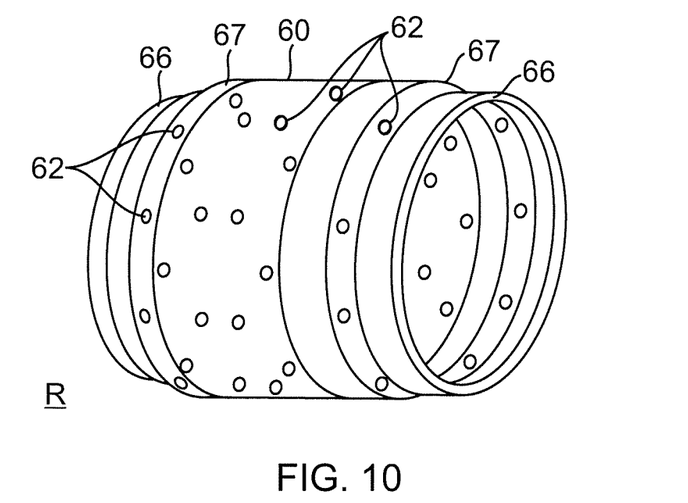
FIG. 10 is a perspective view of an embodiment of an irrigated ring electrode.

A suitable irrigation ring electrode is illustrated in detail in FIG. 10. With reference to FIGS. 6A, 6B, the ring electrode R is adapted for ablation and irrigation. The ring electrodes can be made of any suitable noble metal, such as platinum or gold, preferably a combination of platinum and iridium or gold and platinum. In the illustrated embodiment, the ring electrode is generally cylindrical with a length greater than its diameter. The ring electrode has a side cross-section that can resemble a barrel with a side wall 60 that bulges radially between opposing end portions 66. Curved transitional regions 67 are provided between the side wall 60 and the end portions 66 to provide an atraumatic profile without corners or sharp edges.

With reference to FIGS. 6A, 6B and 6C, a reservoir or annular gap G exists around the exterior of the tubing 49 of the distal portion 19. The gap G provides improved fluid distribution from the lumen 53 to the exterior of the ring electrode via apertures 62. The apertures 62 are arranged the side wall 60 in a predetermined pattern including axially offset rows. These apertures face outwardly promoting flow in a radial direction (see arrows 63). Apertures are also provided in or near the curved transitional regions 67 to promote flow more in an axial direction (see arrows 64). Moreover, these apertures are particularly effective in minimizing charring and coagulation at or near the curved transitional regions 67 which are likely to be "hot spots" resulting from higher current densities due to transitions in the electrode profile. In that regard, the plurality and/or cross-section of the apertures 62 is greater at or near the curved transitional regions 67 than in the side wall 60 of the electrode so as to provide more cooling in the curved transitional regions. Other suitable ring electrodes are described in US Patent Application Publication No. US2010/0168548 A1, and U.S. patent application Ser. No. 13/174,742, filed Jun. 30, 2011, the entire content of both of which are hereby incorporated by reference.

For most PVI applications, the first predetermined length L1 is greater than the diameter of the ostium 30. Thus, the length ranges between about 25 mm and 10 mm, preferably between about 30 mm and 5 mm.

The proximal end of each electrode lead wire is electrically connected to a suitable connector at the distal end of the control handle 16 for connection to an RF generator (not shown). A pair of wires 40, 41 is provided for each electrode. In the disclosed embodiment, wire 40 of the wire pair is a copper wire, e.g. a number "40" copper wire and the wire 41 is a constantan wire. The wires of each pair are electrically isolated from each other except at their distal ends where they are twisted together. Attachment to the respective ring electrode R is accomplished by feeding the wire pair through a hole 140 formed in the side wall into the first lumen 51 of the tubing 49 of the distal assembly 17, and soldering to the respective ring electrode (see FIG. 6A). The wire pairs for each electrode extend distally from the control handle 16, through the central lumen 18 of the catheter body 12, the first lumen 33 of the intermediate section 14, and the first lumen 51 of the distal assembly 17. RF energy, is delivered to the electrodes via the wire 40 of the wire pairs. However, as understood by one of ordinary skill in the art, the wire pairs inclusive of their respective constantan wire can also function as temperature sensors or thermocouples sensing temperature of each electrode.

All of the wire pairs pass through a common nonconductive protective sheath 42 (FIG. 4A), which can be made of any suitable material, e.g., polyimide, in surrounding relationship therewith. The sheath 42 extends from the control handle 16, the catheter body 12, the intermediate section 14, and terminates just proximally of the proximal end of the distal assembly 17. The distal end is anchored in the first lumen 51 by glue, for example, polyurethane glue or the like.

The pair of deflection puller wire 44a, 44b are provided for deflection of the intermediate shaft 14. The puller wires 44a, 44b extend through the central lumen 18 of the catheter body 12 and each through a respective one of the lumens 35 and 36 of the intermediate section 14. They are anchored at their proximal ends in the control handle 16, and at their distal end to a location at or near the distal end of the intermediate section 14 by means of T-bars 142 (FIG. 5B) that are affixed to the sidewall of the tubing 15 by suitable material 103, e.g., polyurethane, as generally described in U.S. Pat. No. 6,371,955, the entire disclosure of which is incorporated herein by reference. The puller wires are made of any suitable metal, such as stainless steel or Nitinol, and is preferably coated with Teflon® or the like. The coating imparts lubricity to the puller wire. For example, each puller wire has a diameter ranging from about 0.006 to about 0.010 inch.

As seen in FIG. 4B, each puller wire has a respective compression coil 144 in surrounding relation thereto. Each compression coil 144 extends from the proximal end of the catheter body 12 to at or near the proximal end of the intermediate section 14 to enable deflection. The compression coils are made of any suitable metal, preferably stainless steel, and are each tightly wound on itself to provide flexibility, i.e., bending, but to resist compression. The inner diameter of the compression coils is preferably slightly larger than the diameter of a puller wire. The Teflon® coating on the puller wire allows it to slide freely within the compression coil. Within the catheter body 12, the outer surface of the compression coil is covered by a flexible, non-conductive sheath 152, e.g., made of polyimide tubing. The compression coils are anchored at their proximal ends to the outer wall 30 of the catheter body 12 by proximal glue joints and to the intermediate section 14 by distal glue joints.

Within the lumens 35 and 36 of the intermediate section 14, the puller wires 44a, 44b extend through a plastic, preferably Teflon®, puller wire sheath 146 (FIG. 4B), which prevents the puller wires from cutting into the wall of the tubing 15 of the intermediate section 14 when the intermediate section 14 is deflected.

Longitudinal movement of the puller wires 44a, 44b relative to the catheter body 12 for bi-directional deflection is accomplished by appropriate manipulation of the control handle 16. A deflection knob 150 (FIG. 1) is provided on the handle which can be pivoted in a clockwise or counterclockwise direction for deflection in the same direction. Suitable control handles for manipulating more than one wire are described, for example, in U.S. Pat. Nos. 6,468,260, 6,500,167, and 6,522,933 and U.S. application Ser. No. 12/960,286, filed Dec. 3, 2010, the entire disclosures of which are incorporated herein by reference.

In one embodiment, the position sensor 48 includes a plurality of single axis sensors ("SASs") carried on the cable 46 that extends through the first lumen 51 of the distal assembly 17 (FIG. 6A), where each SAS occupies a known or predetermined position along the length of the distal section. The cable 46 extends proximally from the distal assembly 17 through the first lumen 33 of the intermediate section 14, the central lumen 18 of the catheter body 12, and into the control handle 16. Each SAS can be positioned with a known and/or equal spacing separating adjacent SASs. In the disclosed embodiment, the cable carries six SASs that are positioned under each ring electrode for sensing location and/or position of each ring electrode so that the operator can energize selected electrode(s). The SASs enable the electrode assembly to be viewed under mapping systems manufactured and sold by Biosense Webster, Inc., including the CARTO, CARTO XP and NOGA mapping systems. Suitable SASs are described in U.S. application Ser. No. 12/982,765, filed Dec. 30, 2010, the entire disclosure of which is incorporated herein by reference.

Figure 11:
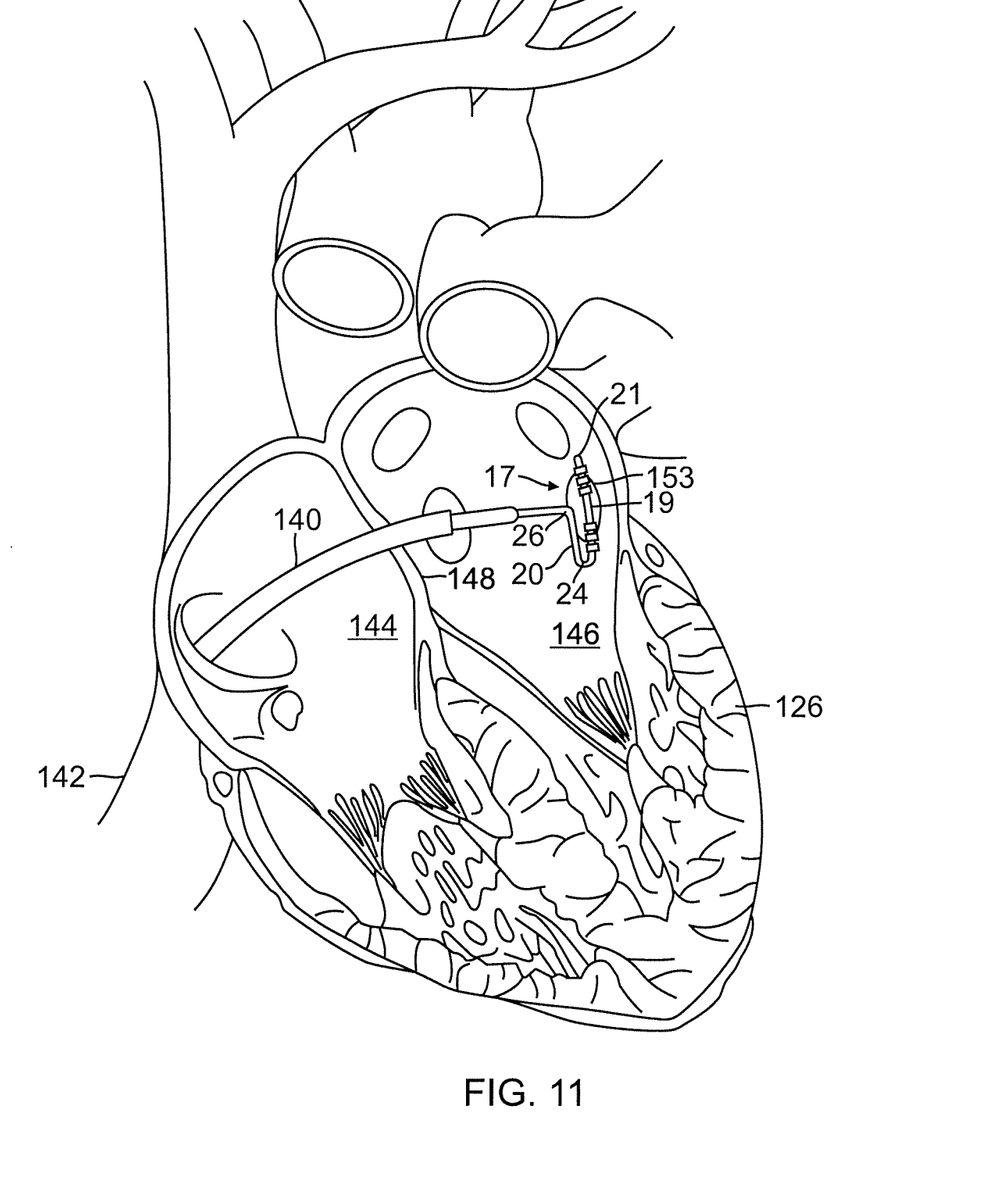
FIG. 11 is a schematic sectional view of a heart showing insertion of a catheter into the left atrium, in accordance with an embodiment of the present invention.

With reference to FIG. 11, an operator, such as a cardiologist, inserts a guiding sheath 140 through the vascular system of the patient so that the distal end of the guiding sheath enters a chamber of the patient's heart 126, for example, the left atrium 146. Operator then advances the catheter through the guiding sheath. The flexible shape memory support member of the electrode assembly 17 readily unfolds, allowing the U-shaped portion 24 and the elbow connecting portion 26 to be opened to at least about 120 degrees so that the free distal end 21 of the distal portion 19 is fed through the guiding sheath, followed by the U-shaped portion 24, the proximal portion 20 and the elbow connecting portion 26. The catheter is fed through the guiding sheath until at least the entirety of the electrode assembly 17 is past the distal end of the guiding sheath whereupon the electrode assembly resumes its shape-memory configuration.

The operator can advance and retract the catheter in the left atrium and deflect the intermediate portion 14 as appropriate to aim the electrode assembly 17 toward a PV ostium 153. The catheter is advanced until the distal linear portion 19 straddles the ostium and comes into contact with the ostium along any chord or a diameter of the ostium. Additional normal force can be applied to depress and/or compress the portion(s) 19 and 20 toward the ostium and/or each other.

Catheter 10 is connected by a suitable connector at its proximal end to a console. The console comprises an RF generator for applying RF energy through selected ring electrode(s) for ablation. If desired, the catheter can be rotated or twirled about its longitudinal axis so that the electrode assembly 17 comes into contact with different locations on the ostium for ablating discreet or continuous lesions.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Any feature or structure disclosed in one embodiment may be incorporated in lieu of or in addition to other features of any other embodiments, as needed or appropriate. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising:
    an elongated body;
    a distal section having an electrode assembly, the electrode assembly including:
        an electrode structure biased into a predetermined generally T-shape in an undeformed state that includes:
            a generally linear distal portion having a first predetermined length sufficient to span an ostium of a pulmonary vein, the generally linear distal portion being generally perpendicular to a longitudinal axis of the elongated body;
            a generally linear proximal portion having a second predetermined length lesser than the first predetermined length and being generally perpendicular to the longitudinal axis of the elongated body;
            a U-shaped portion between the generally linear distal portion and the generally linear proximal portion;
            an elbow connecting portion proximal of the generally linear proximal portion, wherein the generally linear distal and proximal portions, the U-shaped portion, and the elbow connecting portion generally lie within a single common plane; and
        at least two ring electrodes on the generally linear distal portion; and
    a control handle proximal of the elongated body.

2. A catheter of claim 1, wherein the generally linear distal portion has a free distal end.

3. A catheter of claim 1, wherein the electrode assembly includes a support structure with shape memory.

4. A catheter of claim 1, wherein the elbow connecting portion spans an angle generally ranging between about 30 and 120 degrees.

5. A catheter of claim 1, wherein the second predetermined length is about 50% of the first predetermined length.

6. A catheter of claim 1, wherein the second predetermined length is about 25% of the first predetermined length.

7. A catheter of claim 1, wherein the second predetermined length is about 75% of the first predetermined length.

8. A catheter of claim 1, further comprising an intermediate deflection section between the elongated body and the distal section.

9. A catheter of claim 1, wherein the generally linear distal portion carries a distal group of ring electrodes and a proximal group of ring electrodes.

10. A catheter of claim 9, wherein each of the distal group and the proximal group of ring electrodes has at least two ring electrodes.

11. An ablation catheter comprising:
    an elongated body;
    a distal section having an electrode assembly, the electrode assembly including:
        an electrode structure biased into a predetermined generally T-shape in an undeformed state that includes;
            a generally linear distal portion having a first predetermined length sufficient to span an ostium of a pulmonary vein, the generally linear distal portion being generally perpendicular to a longitudinal axis of the elongated body;
            a generally linear proximal portion having a second predetermined length lesser than the first predetermined length and being generally perpendicular to the longitudinal axis of the elongated body;
            a U-shaped portion between the generally linear distal portion and the generally linear proximal portion;
            an elbow connecting portion proximal of the generally linear proximal portion, wherein the generally linear distal and proximal portions, the U-shaped portion and the elbow connecting portion generally lie within a single common plane; and
        at least a distal ring electrode and a proximal ring electrode on the generally linear distal portion; and
    a control handle proximal of the elongated body,
    wherein the generally linear distal portion has a proximal end and a distal end and is adapted for generally simultaneous contact between a proximal ring electrode at or near the proximal end and one location on an ostium and between a distal ring electrode at or near the distal end and another location on the ostium.

12. A catheter of claim 11, wherein the generally linear distal portion has a free distal end.

13. A catheter of claim 11, wherein the electrode assembly includes a support structure with shape memory.

14. A catheter of claim 11, wherein the elbow connecting portion spans an angle generally ranging between about 30 and 120 degrees.

15. A catheter of claim 11, wherein the second predetermined length is about 50% of the first predetermined length.

16. A catheter of claim 11, wherein the generally linear distal portion carries a distal group of ring electrodes and a proximal group of ring electrodes.

17. A catheter of claim 16, wherein each of the distal group and the proximal group of ring electrodes has at least two ring electrodes.

* * * * *